United States Patent [19]

Green et al.

[11] Patent Number: 5,336,232
[45] Date of Patent: Aug. 9, 1994

[54] APPROXIMATING APPARATUS FOR SURGICAL JAW STRUCTURE AND METHOD OF USING THE SAME

[75] Inventors: David T. Green, Westport; Henry Bolanos, East Norwalk; Jeffrey J. Blewett, Plantsville; Keith Ratcliff; Frank J. Viola, both of Sandy Hook; Charles R. Sherts, Southport, all of Conn.

[73] Assignee: United States Surgical Corporation, Norwalk, Conn.

[21] Appl. No.: 7,410

[22] Filed: Jan. 22, 1993

Related U.S. Application Data

[63] Continuation of Ser. No. 669,352, Mar. 14, 1991, abandoned.

[51] Int. Cl.$^5$ .............................................. A61B 17/28
[52] U.S. Cl. .................................... 606/151; 606/205; 128/774; 227/181; 81/355; 81/359
[58] Field of Search ............... 606/151, 157, 158, 201, 606/205–208; 128/774, 20; 227/178, 175, 181; 81/352–355, 359

[56] References Cited

U.S. PATENT DOCUMENTS

| | | |
|---|---|---|
| 984,756 | 2/1911 | Frisch .............................. 606/207 X |
| 1,517,302 | 12/1924 | McNerney ........................ 81/352 X |
| 1,659,112 | 2/1928 | Littlejohn .......................... 606/205 |
| 1,717,726 | 6/1929 | McGill ................................... 81/352 |
| 2,034,785 | 3/1936 | Wappler . |
| 3,232,150 | 2/1966 | Allegraud .......................... 81/355 X |
| 3,269,630 | 8/1966 | Fleischer . |
| 3,506,012 | 4/1970 | Brown . |
| 3,618,842 | 11/1971 | Bryan . |
| 3,795,034 | 8/1974 | Strekopytov et al. . |
| 3,828,791 | 8/1974 | Santos ................................... 606/207 |
| 3,844,289 | 10/1974 | Noiles . |
| 3,866,610 | 2/1975 | Kletschka . |
| 3,895,636 | 7/1975 | Schmidt . |
| 4,038,987 | 8/1977 | Komiya . |
| 4,106,508 | 8/1978 | Berlin . |
| 4,122,855 | 10/1978 | Mosior et al. . |
| 4,169,476 | 10/1979 | Hiltebrandt . |
| 4,171,701 | 10/1979 | Walter et al. . |
| 4,226,024 | 10/1980 | Westerberg et al. . |
| 4,233,743 | 11/1980 | Flick ................................. 128/774 X |
| 4,243,047 | 1/1981 | Olsen . |
| 4,265,021 | 5/1981 | Campbell . |
| 4,312,363 | 1/1982 | Rothfuss et al. . |
| 4,319,576 | 3/1982 | Rothfuss . |
| 4,369,788 | 1/1983 | Goald . |
| 4,424,811 | 1/1984 | Groot . |
| 4,442,964 | 4/1984 | Becht . |
| 4,512,343 | 4/1985 | Falk et al. . |
| 4,536,960 | 8/1985 | Muti . |
| 4,566,620 | 1/1986 | Green et al. . |
| 4,572,185 | 2/1986 | Rich . |
| 4,580,712 | 4/1986 | Green . |
| 4,590,936 | 5/1986 | Straub et al. . |
| 4,603,693 | 8/1986 | Conta et al. . |
| 4,646,751 | 3/1987 | Maslanka . |
| 4,674,501 | 6/1987 | Greenberg . |
| 4,711,240 | 12/1987 | Goldwasser et al. ............. 81/352 X |
| 4,714,187 | 12/1987 | Green . |
| 4,728,020 | 3/1988 | Green et al. . |
| 4,760,848 | 8/1988 | Hasson . |
| 4,788,978 | 12/1988 | Strekopytov et al. . |
| 4,873,771 | 10/1989 | Wust . |
| 4,931,058 | 6/1990 | Cooper . |
| 4,976,721 | 12/1990 | Blasnik et al. . |
| 4,994,079 | 2/1991 | Genese et al. . |
| 5,100,042 | 3/1992 | Gravener et al. ............. 227/178 X |

FOREIGN PATENT DOCUMENTS

| | | |
|---|---|---|
| 0092300 | 10/1983 | European Pat. Off. . |
| 0211114 | 2/1987 | European Pat. Off. . |
| 0406724 | 1/1991 | European Pat. Off. . |
| 268621 | 6/1989 | Fed. Rep. of Germany ...... 606/201 |
| 70697 | 3/1916 | Switzerland ...................... 606/207 |
| 1456108 | 2/1989 | U.S.S.R. ........................... 606/201 |

OTHER PUBLICATIONS

European Search Report.

*Primary Examiner*—Michael H. Thaler

[57] ABSTRACT

Approximating apparatus for surgical jaw structure is provided which effects substantially parallel approximation of first and second surgical jaw structure to permit substantially parallel working interaction therebetween. The approximating apparatus includes camming structure for engaging at least one movable jaw of the surgical jaw structure to bias that jaw toward or away from a second jaw structure in a substantially parallel manner.

15 Claims, 8 Drawing Sheets

FIG. 11

APPROXIMATING APPARATUS FOR SURGICAL JAW STRUCTURE AND METHOD OF USING THE SAME

This is a continuation of copending application Ser. No. 07/669,352 filed on Mar. 14, 1991, now abandoned.

BACKGROUND OF THE INVENTION

1. Field of the Invention

The present invention relates generally to approximating apparatus for surgical instrumentation and more particularly to apparatus which effects substantially parallel approximation of the jaw structure for surgical instrumentation.

2. Description of the Related Art

A wide variety of surgical procedures used today involve surgical instrumentation having jaw structure such as, for example, grippers, graspers, dissectors, clamps, 5 cutting elements, stapling elements and tissue measuring devices. In each of these types of jaw structure affected tissue is captured by the jaws for manipulation. The ease and accuracy of this tissue capturing step is extremely important if the surgical procedure is to be carried out in an efficient manner. One type of jaw structure currently used captures tissue by a pivotal action of the jaw structure wherein the jaws close progressively from a pivot point outward to the end of the jaw structure. See, for example U.S. Pat. Nos. 3,866,610; 4,243,047; 4,369,788; 4,512,343; 4,572,185; 4,590,936 and 4,674,501. This pivotal action can, in certain circumstances, overcompress captured tissue nearest to pivot point while undercompressing captured tissue near the ends of the jaw structure. The uneven compression can result in uneven cutting, unintentional tissue trauma, and/or inaccurate tissue measurement or joining. This is particularly true in endoscopic or laparoscopic procedures where accessibility is extremely limited. In these procedures accuracy and precision are vitally important. Apparatus must be capable of easily and accurately capturing tissue for subsequent manipulation without unintentional trauma.

A more accurate and atraumatic way of approximating surgical jaw structure is by parallel approximation. This approach has been utilized with some success in the area of surgical clamping. For example, in U.S. Pat. Nos. 4,931,058 (Cooper) and 4,976,721 (Blasnik et al.) surgical clamp structure is shown wherein spring loaded parallel clamping jaws are moved together in parallel orientation by compression of locking structure disposed on an end of the jaw structure. These surgical clamps however are not readily operable in remote or limited visibility applications such as, for example, endoscopic or laparoscopic procedures and do not make use of camming action.

Similarly, some surgical stapler designs make use of parallel approximation to facilitate capture and joining of tissue. For example, U.S. Pat. Nos. 3,269,630; 3,795,034; 4,319,576; 4,442,964; 4,603,693; 4,788,978 and 4,930,503 disclose some degree of parallel approximation of anvils and staple cartridge elements. However, these designs are somewhat bulky and in some cases difficult to manipulate. U.S. Pat. No. 3,844,289 shows a scissors type hemostat having L-shaped jaw structure for capturing tissue therebetween. A clip applier is attached to the hemostat for clipping the captured tissue. In operation, the clip applier moves substantially perpendicular to the plane of the working ends of the hemostat jaw structure by means of pins and slots to clip the captured tissue. None of these references utilize camming structure or a camming action to effect substantially parallel approximation of surgical jaw structure while maintaining an efficient and simple mode of operation for the working ends thereof.

Therefore, it would be highly desirable to have approximating jaw structure for surgical instrumentation which allows for accurate and precise substantially parallel approximation in remote or limited accessibility applications.

Accordingly, it is an object of the present invention to provide apparatus for approximating jaw structure which provides accurate substantially parallel capture of subject tissue.

Another object of the present invention is to provide apparatus for approximating jaw structure for surgical instrumentation which permits parallel approximation of jaw structure on subject tissue in remote or limited accessibility conditions.

Other and further objects of the present invention will be explained hereinafter, and will be more particularly delineated in the appended claims, and other objects of the present invention will hereinafter become apparent to one with ordinary skill in the art to which the present invention pertains.

SUMMARY OF THE INVENTION

The present invention is an approximating apparatus for jaw structure in surgical instrumentation such as, for example, grippers, graspers, dissectors, cutters, measurers, staplers, etc. This approximating apparatus effects substantially parallel approximation of first and second surgical jaw structure to permit substantially parallel working interaction therebetween. The approximating apparatus includes camming structure engaging at least one movable jaw of the surgical jaw structure to bias that jaw structure toward a second jaw structure. In one embodiment, a camming plate is provided with parallel diagonal camming slots formed therein. The camming plate is axially disposed in a housing or frame mounting a stationary surgical jaw structure. A movable jaw structure is mounted in the housing for substantially parallel movement perpendicular to the plane of the stationary surgical jaw structure. The movable jaw structure is blocked against axial movement within the housing. Camming pins, attached to the movable jaw structure, ride in the parallel diagonal camming slots in the camming plate. As the camming plate is moved axially within the housing, the movable jaw structure moves perpendicular to the plane of the stationary jaw structure into parallel approximation with the stationary jaw structure.

Other camming structure may be utilized within the scope of the present invention to achieve substantially parallel approximation of a movable surgical jaw structure relative to a stationary surgical jaw structure. For example, camming surfaces may be provided on the movable surgical jaw structure which are engaged by a camming tube adapted for distal and proximal axial movement around at least a portion of the movable and stationary surgical jaw structure. The camming surfaces on the camming tube engage the camming surfaces on the movable surgical jaw structure to move it in substantially parallel approximation in a direction perpendicular to the longitudinal plane of the stationary surgical jaw structure.

In particularly advantageous embodiments of the present invention, the camming surfaces and or slots may be angled for example to widen the initial distal spacing of the surgical jaw structure to assist in the capture of tissue. Also, it is contemplated that the approximating apparatus for the surgical jaw structure can be formed as a separate removable unit for interchangability with various types of actuating means. For example, approximating tissue measuring jaws could be removed from an actuating means and replaced with stapling jaws or cutting jaws, etc.

BRIEF DESCRIPTION OF THE DRAWINGS

For a further understanding of the objects of the present invention, reference is made to the following detailed description of preferred embodiments which is to be taken in connection with the accompanying drawings, wherein.

DETAILED DESCRIPTION OF PREFERRED EMBODIMENTS

Figure 1:
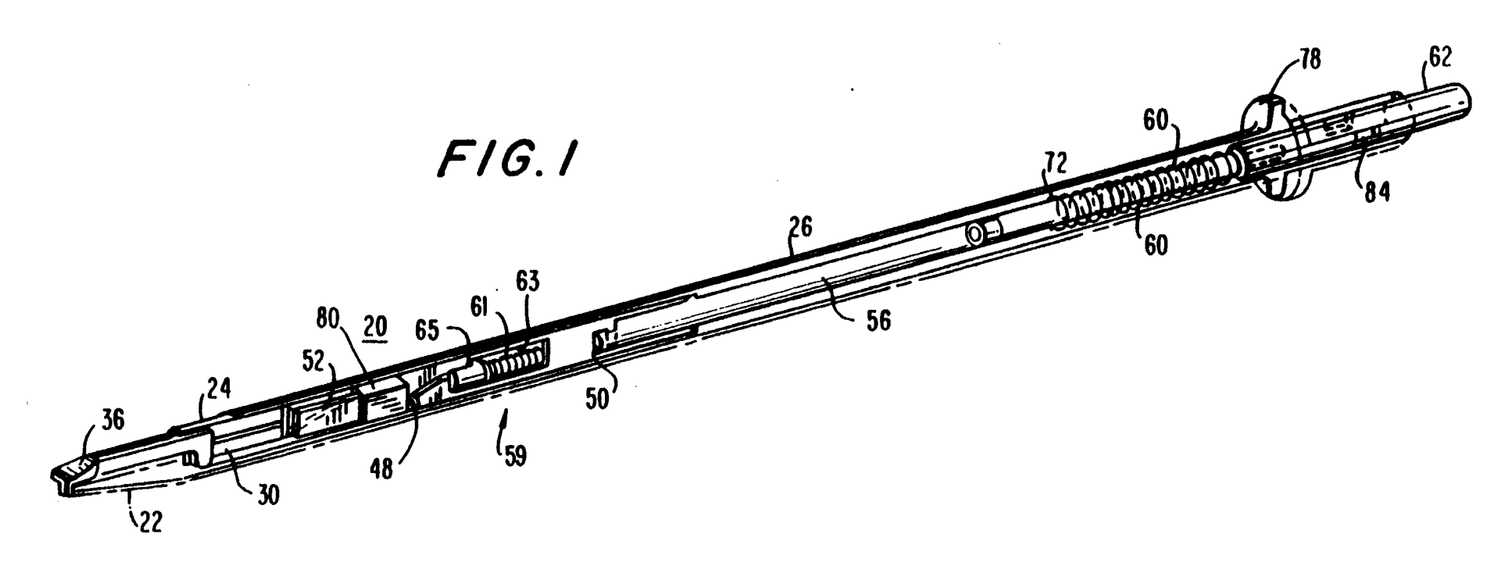
FIG. 1 is a perspective view in cross section of an apparatus in accordance with the present invention utilizing tissue measuring jaw structure shown in the closed approximated position.
Figure 2:
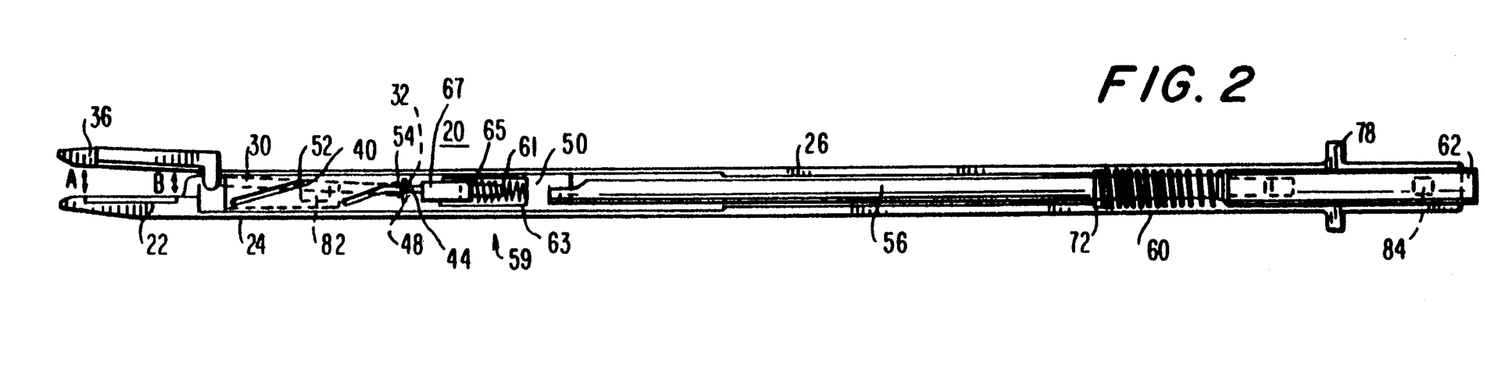
FIG. 2 is a side view in cross section of the apparatus of FIG. 1 showing the tissue measuring jaw structure in the open position.
Figure 3:
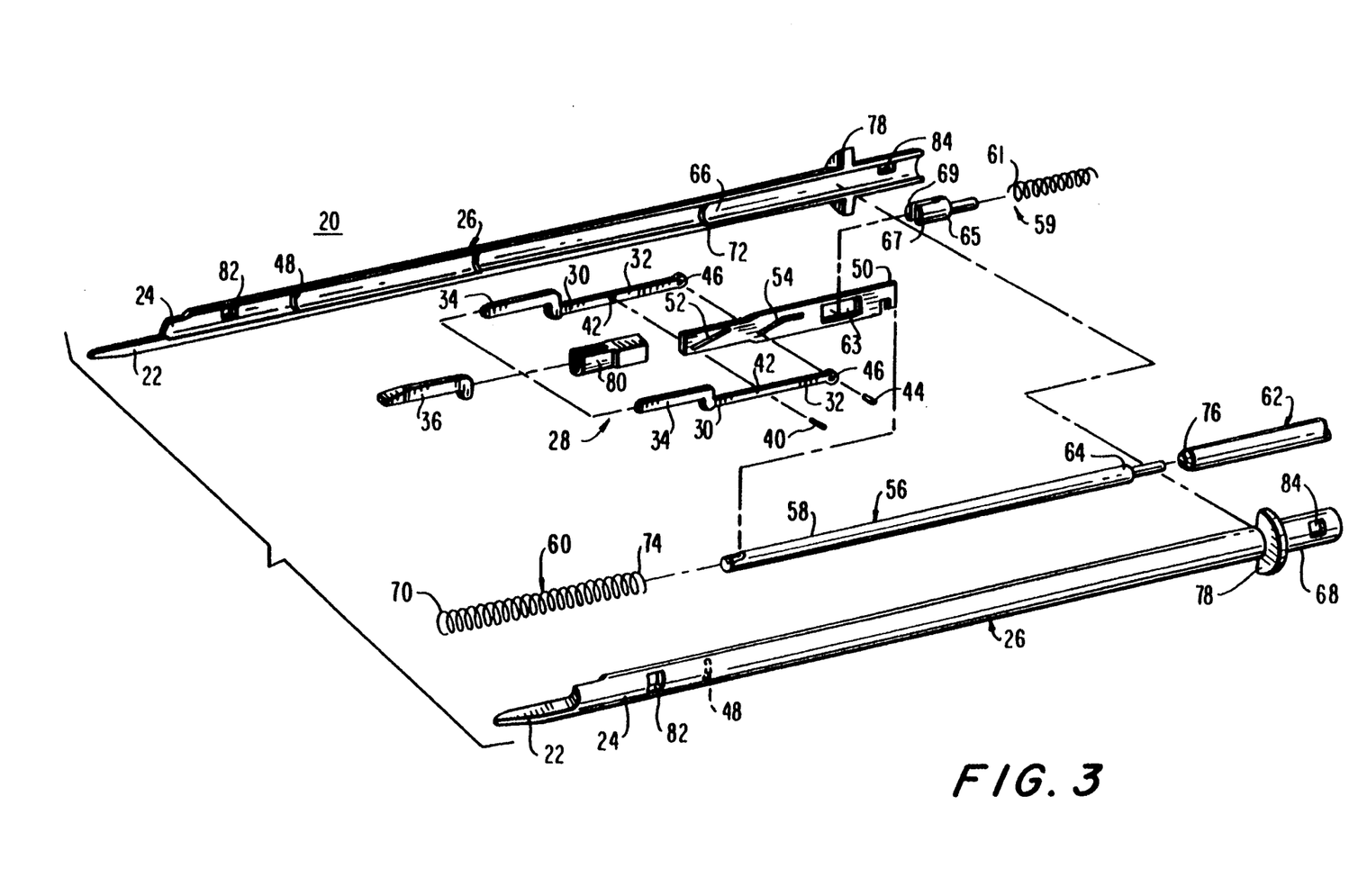
FIG. 3 is an exploded perspective view of the tissue measuring apparatus of FIG. 1.

Referring to FIGS. 1-14 wherein like parts have been given like index numerals and initially to FIGS. 1-3, there is shown approximating apparatus in accordance with a preferred embodiment of the present invention for use in endoscopic tissue measuring instrumentation 20. A stationary first jaw structure 22 is integrally formed on a distal end 24 of tubular housing or frame means 26 in axial alignment therewith. A second movable jaw structure 28 is movably retained by the tubular frame means 26 for substantially parallel approximation with the stationary first jaw structure 22. Second movable jaw structure 28 comprises a pair of dog leg frame members 30 having proximal and distal ends 32, 34. A jaw sleeve 36 overfits both distal ends 34 of the dog leg frame member 30 and assists in holding the members together. The proximal ends 32 are disposed parallel to one another and define a yoke therebetween. A first camming pin 40 is inserted through opposing transverse bores 42 formed in the proximal ends 32 of the dog leg frame members 30 and is flush with the outer surface of the dog leg frame members 30. A second camming pin 44 is inserted in opposing transverse bores 46 formed proximal to opposing bores 42 in the proximal ends 32 of the dog leg frame members 30. Second camming pin 44 extends transversely beyond the outer surface of the dog leg frame members 30 and engage a pair of perpendicular grooves 48 formed in the side walls of tubular frame means 26. This second camming pin 44 prevents longitudinal motion of the second movable jaw structure 28 relative to stationary jaw structure 22 and serves to assist in guiding the second jaw structure 28 in substantially parallel approximation with the stationary jaw structure 22.

A camming plate 50 having first and second camming slots 52, 54 is axially positioned in the yoke formed by the proximal ends 32 of dog leg frame members 30 for longitudinal movement therethrough. First and second camming pins 40, 44 are disposed in first and second camming slots 52, 54 for longitudinal angular movement therein. In the embodiment shown in FIGS. 1-3 first and second camming slots 52, 54 extend diagonally and remain substantially parallel for approximately half of their height. Thereafter, second camming slot 54 extends in a plane substantially parallel to the longitudinal axis of tubular frame means 26 while first camming slot 52 continues diagonally. This feature permits the opening between the distal ends of the first and second jaw structure "A" to be overextended with respect to the opening at the proximal portion of the jaw structure "B". Thus, initial capture of tissue is facilitated by the widened jaw orientation. Thereafter, the jaw structure will reorient to substantially parallel alignment to permit substantially parallel approximation and working interaction between the jaws.

In the embodiment of FIGS. 1-3 the tissue measuring device 20 is normally oriented with the jaw structure in the closed approximated position (see FIG. 1). The actuating mechanism for effecting longitudinal movement of camming plate 50 and thus the substantially parallel movement of jaw structure 28 relative to jaw structure 22 includes a shaft 56 attached at a distal end 58 to a proximal end of camming bar 50, a compression spring 60 and plunger 62 attached to a proximal end 64 of shaft 56. A longitudinal cavity 66 is dimensioned and configured in a proximal end 68 of tubular housing 26 to retain compression spring 60. A distal end 70 of compression spring 60 abuts annular step 72 formed in the tubular frame means 26 while the proximal end 74 of compression spring 60 contacts the distal end 76 of plunger 62.

Distal longitudinal movement of plunger 62 compresses spring 60 and drives shaft 56 axially within tubular frame means 26. A circumferential flange 78 is formed around the outside of the proximal end 68 of the tubular frame means 26 to assist in compression of plunger 62. Camming bar 50 is driven in a distal longitudinal direction causing first and second camming pins 40, 44 to ride in first and second camming slots 52, 54 respectively to open jaw structure 28 relative to stationary jaw structure 22. Since second camming pin 44 is restricted from axial movement by perpendicular grooves 48, jaw structure 22 and 28 move apart in a substantially parallel orientation. Once the tissue is captured within the jaws 22, 28, the plunger 62 is released and compression spring 60 serves to reverse the longitudinal direction of shaft 56 causing the jaws to close on the tissue. The force of compression spring 60 is selected to provide an accurate measurement of tissue thickness, i.e., so as not to cause undue tissue compression.

Where relatively thick tissue (i.e. thicker than about 0.1 inch) is to be captured and measured, supplemental approximation assist means may be incorporated to assure quick and accurate measurement. In the embodiment of FIGS. 1-3, supplemental approximation assist means, shown generally at 59, is positioned in slot 63 formed in camming plate 50 and includes a secondary compression spring 61 and fork 65. Both spring 61 and fork 65 are dimensioned and configured to fit longitudinally within slot 63 with arms 67, 69 of fork 65 extending distally beyond slot 63 to abut and engage the proximal ends 32 of dog leg frame members 30 as necessary. The force of secondary compression spring 61 is selected so as to provide supplemental approximation assistance to compression spring 60 when thick tissue is to be measured. Thus, as shown in FIGS. 1 and 2, when the endoscopic tissue measuring instrument 20 is closed or approximated around relatively thin tissue (FIG. 1), arms 67, 69 of fork 65 do not engage the proximal ends 32 of dog leg frame members 30. However, referring to FIG. 2, as the second jaw structure 28 is opened relative to first jaw structure 22, the proximal ends 32 of dog leg frame members 30 engage the arms 67, 69 of fork 65 and serve to compress secondary spring 61 in slot 63. When capture of tissue is completed, the combined expansion forces of compression spring 60 and secondary compression spring 61 serve to approximate jaw structures 22 and 28 to provide a quick and accurate measurement of the captured tissue. One skilled in the art will readily appreciate that other types of approximation assist means may be incorporated to assist as necessary in the closure of surgical jaw structure and that such assist means may be adapted to engage and/or assist in closure during any stage of approximation or separation of the surgical jaw structure.

In the embodiment shown in FIGS. 1-3 visual measurement apparatus is incorporated into both the proximal and distal ends of tubular frame means 26. At the distal end, a measuring jacket 80 is positioned over dog leg frame members 30 and gauges the vertical position of movable second jaw structure 28 relative to first jaw structure 22. A window 82 is provided in tubular frame means 26 adjacent measuring jacket 80 to facilitate reading the measurement. Graduations may be provided on jacket 80 which translate into thickness measurements of the captured tissue. At the proximal end of tubular frame means 26 a second window is provided to accurately determine the axial position of plunger 62 relative to frame means 26. Graduations may be provided on plunger 62 which translate into thickness measurements of the captured tissue.

This embodiment of the approximating apparatus utilized in a tissue measuring configuration is designed to measure the thickness of tissue captured between the jaw structure 22, 28. One skilled in the art will readily appreciate that the instrumentation can be configured to make other tissue measurements such as, for example, inner diameters of hollow body organs simply by utilizing the outer surfaces of the jaw structure as the measuring point. Thus the jaw would be inserted into the hollow organ and expanded in a substantially parallel manner until the outer surfaces of the jaw structure contacts the inner surface of the hollow organ. A measurement of the inner diameter of that organ can then be generated.

Various known actuating mechanisms may be utilized to drive camming plate 50 including, for example, axial screw type structure, folding handles, scissors or pistol grip type structures capable of effecting axial longitudinal movement of the camming bar. Further, the tissue measuring device 20 shown in FIGS. 1-3 is designed and configured for advantageous use in endoscopic or laparoscopic procedures wherein the tubular frame means 26 is inserted through a cannula for manipulation inside an enclosed body cavity. Various other housing configurations are possible for use not limited to insertion through a cannula. These housing configurations are within the scope of one skilled in the art.

Figure 4:
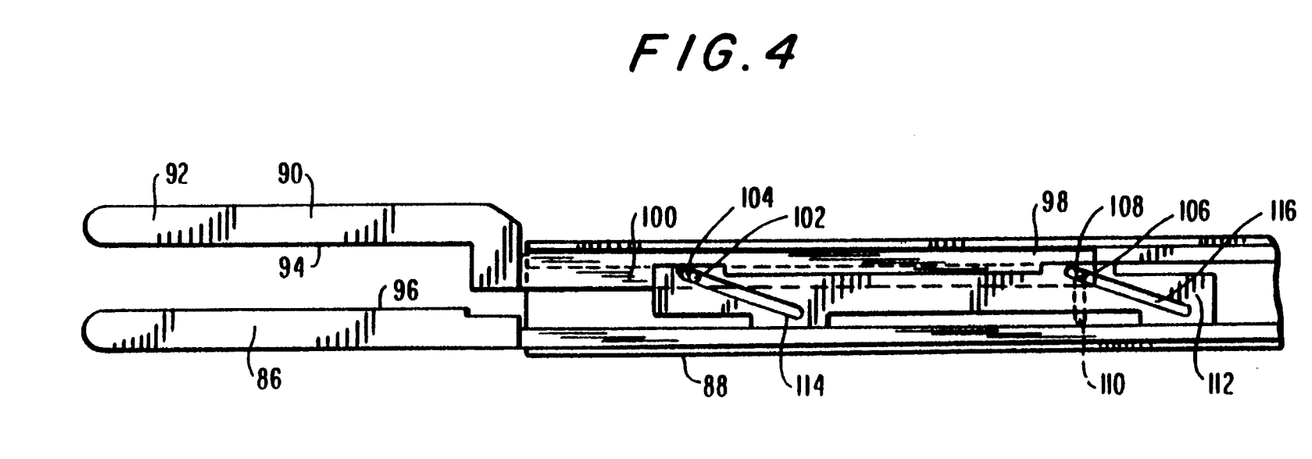
FIG. 4 is a side view in partial cross section of apparatus in accordance with the present invention utilizing surgical clamping jaw structure shown in the open position.

Referring to FIG. 4, an approximating apparatus in accordance with the present invention is shown in conjunction with surgical clamping jaw structure. This approximating apparatus is substantially similar to that discussed above with respect to the tissue measuring device. A stationary first surgical clamping jaw 86 is attached to housing or frame 88. A movable second surgical clamping jaw 90 is retained in housing 88 for substantially parallel approximation toward stationary first surgical clamping jaw 86. The second surgical clamping jaw 90 comprises a distal end 92 having a working clamping surface 94 formed on an inner surface thereof matable in opposing relation to a corresponding working clamping surface 96 formed on an inner surface of the stationary first surgical clamping jaw 86. The proximal end 98 of the second surgical clamping jaw 90 forms two parallel longitudinal arms 100 forming a yoke therebetween. A first camming pin 102 is inserted through opposing transverse bores 104 formed in the parallel longitudinal arms 100 of the second surgical clamping jaw 90. A second camming pin 106 is inserted through opposing transverse bores 108 formed in the parallel longitudinal arms 100 of the second surgical clamping jaw 90 proximal of opposing bores 104. At least one of the camming pins 102, 104 is positioned within perpendicular parallel grooves 110 formed in the sidewalls of frame means 88 to prevent axial movement of the second surgical clamping jaw 90 relative to the first surgical clamping jaw 86.

A camming bar 112 having first and second camming slots 114 and 116 is axially positioned in the yoke formed by parallel longitudinal arms 100 for longitudinal movement therethrough. First and second camming pins 102, 106 are disposed in first and second camming slots 114, 116 respectively for longitudinal angular movement therein. In the approximating apparatus of FIG. 4, camming slots 114 and 116 extend diagonally and remain substantially parallel throughout their length. Thus, in this configuration the first and second surgical clamping jaws remain substantially parallel throughout their range of relative movement.

In operation, an appropriate actuating mechanism (not shown) is engaged to drive camming bar 112 in a longitudinal distal direction. This longitudinal distal movement of the camming bar 112 causes first and second camming pins 102, 106 to move in parallel diagonal camming slots 114, 116 causing the substantially parallel approximation of the second surgical clamping jaw relative to the first.

Figures 5, 6:
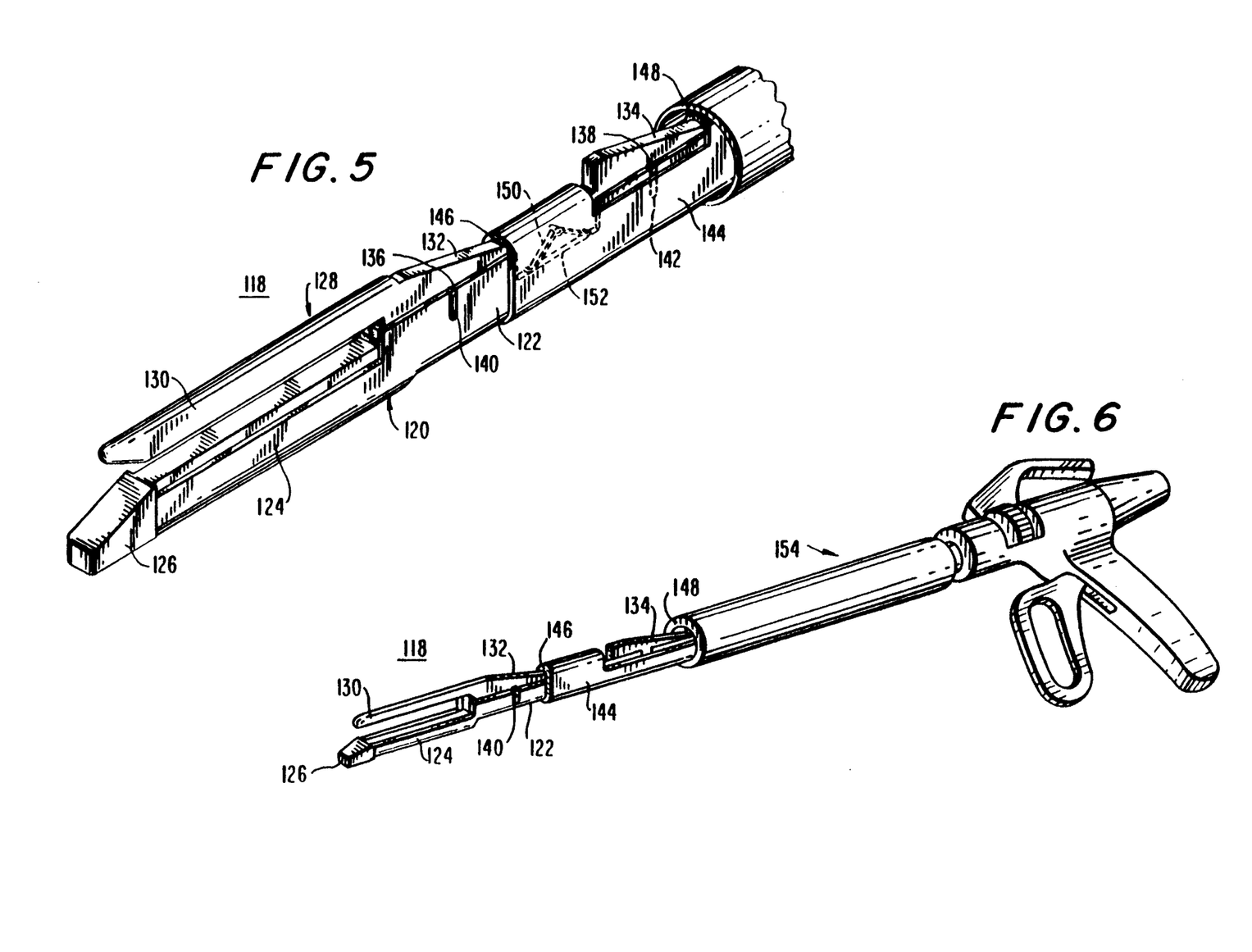
FIG. 5 is a perspective view of apparatus in accordance with the present invention utilizing surgical stapling jaw structure shown in the open position.
FIG. 6 is a side view of the apparatus of FIG. 5 removably attached to an actuating device.

The apparatus of FIGS. 5-6 utilizing surgical stapling working ends may advantageously be used in conjunction with the tissue measuring device of FIGS. 1-3, particularly where both the tissue measuring and stapling devices are interchangable with and actuatable by a single actuating means. For example, prior to stapling, the tissue measuring device of FIGS. 1-3 is inserted onto an appropriate actuating means and used to capture tissue and generate a size measurement thereof. Based on that generated measurement, a staple size is selected which will accurately and efficiently join the tissue. Thereafter, the surgical stapling jaw structure having a staple cartridge therein with staples of a preselected size is inserted onto the actuating means and positioned to staple the tissue.

It is readily apparent to one skilled in the art that the angular configuration of the camming slots 114 and 116 may be varied, either collectively or individually, to achieve different substantially parallel approximation sequences. For example, as shown in FIGS. 1-3 above, one slot may be configured to allow for an initially wider opening at the distal ends of the jaws to facilitate capture of tissue. It is possible to orient the slot configurations at a different angle to close the distal ends of the jaws first, prior to final approximation, in order to avoid loss of the captured tissue out of the distal end.

Referring now to FIGS. 5-6, approximating apparatus in accordance with the present invention is shown configured for use in a surgical stapler device shown generally at 118. A first stationary jaw structure 120 comprises a substantially U-shaped channel having a proximal end 122 and a distal end 124. A staple cartridge 126 is positioned within the U-shaped channel at the distal end of the first stationary jaw structure 120. Second movable jaw structure 128 comprises an anvil 130 formed on a distal end and a first and second sloped camming surface 132, 134 formed on an upper portion of a proximal end thereof. The first and second jaw structure are interconnected by means of a pair of transverse pins 136, 138 which extend through the proximal end of second movable jaw structure 128, which pins are retained in two pairs of corresponding vertical parallel slots 140, 142 formed in vertical side walls of the proximal end 122 of the first stationary jaw structure 120. Thus the second movable jaw structure 128 fits within the U-shaped channel of first stationary jaw structure 120 for substantially parallel reciprocal motion therein.

A camming housing or frame 144 surrounds the respective proximal ends of the first and second jaw structure 120, 128 and is mounted for longitudinal reciprocal motion relative to the jaw structure. First and second camming surfaces 146, 148 are formed in an upper portion of the camming housing 144 and respectively engage first and second sloped camming surfaces 132, 134 formed in the proximal end of second jaw structure 128. A leaf spring 150 is positioned between the first and second camming surfaces 132, 134 and engages a shelf 152 formed in a vertical side wall of the proximal end of the first stationary jaw structure 120. This leaf spring 150 serves to bias apart the respective distal ends of the first and second jaw structure 120, 128.

In operation, an actuating means, shown generally at 154 in FIG. 6, is activated to move camming housing 144 in a distal longitudinal direction relative to the first and second jaw structure 120, 128. This action causes first and second camming surfaces 146, 148 on the camming housing 144 to respectively engage first and second sloped camming surfaces 132, 134 on the proximal end of the second movable jaw structure 128. Since transverse pins 136, 138 in vertical parallel slots 140, 142 allow for only substantially parallel approximating motion, the second movable jaw structure 128 is moved in a substantially parallel fashion relative to first stationary jaw structure 120 resulting in approximation of anvil 130 and staple cartridge 126. Once tissue to be stapled is captured and the jaws are approximated, the staples can be fired and tissue cut using known structure and techniques.

In the apparatus shown in FIGS. 5-6, the first and second jaw structure 120, 128 and the camming housing 144 are formed as a unit and are removable from the actuating means 154 simply by applying a longitudinal distal force sufficient to disengage the unit therefrom. Thus, a wide variety of different types of jaw structure, i.e. clamps (FIG. 4), tissue measurers (FIG. 1), grippers (FIG. 7), etc., may be utilized with a single actuating means.

Figure 7:
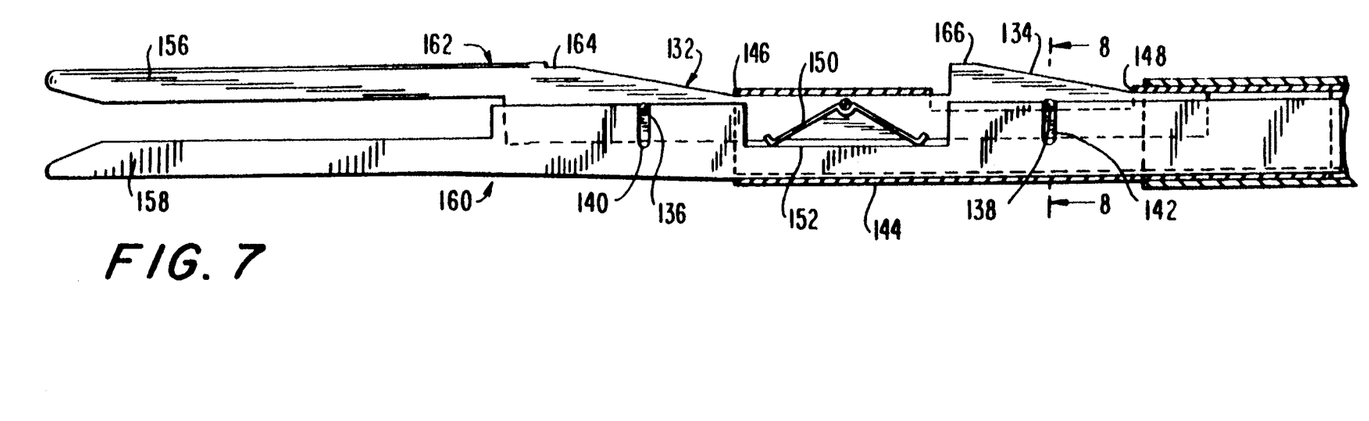
FIG. 7 is a side view in cross section of apparatus in accordance with the present invention utilizing surgical gripping jaw structure shown in the open position.
Figure 8:
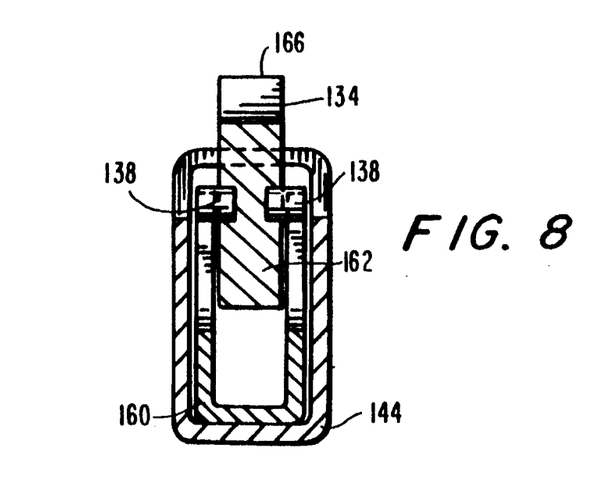
FIG. 8 is an end view of the apparatus of FIG. 7 along line 8—8.
Figure 9:
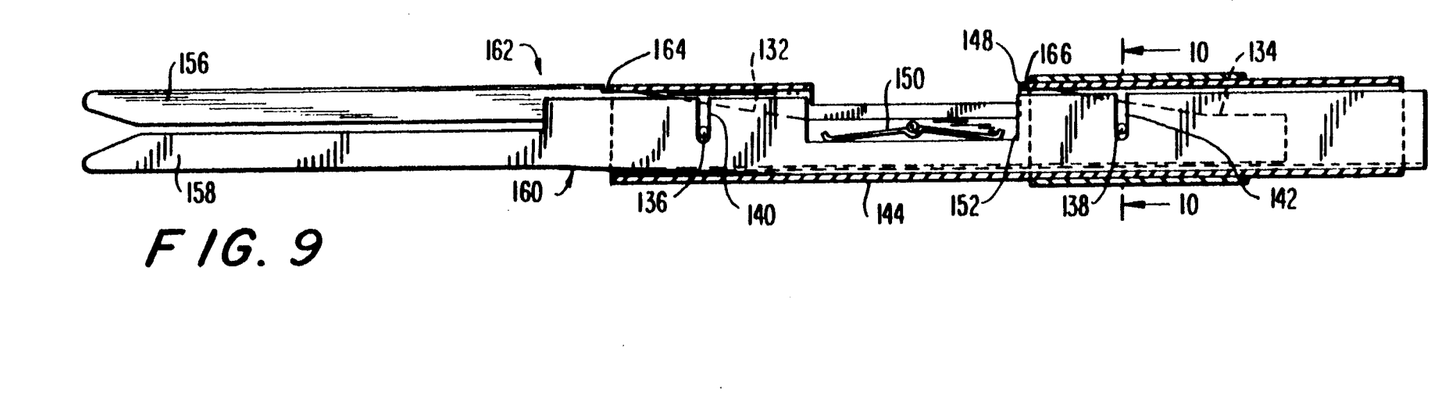
FIG. 9 is a side view in cross section of apparatus in accordance with the present invention as in FIG. 7 shown in the closed position.
Figure 10:
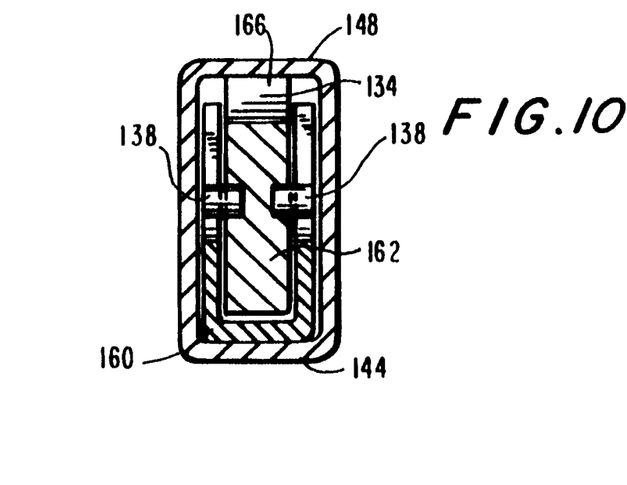
FIG. 10 is an end view in cross section of the apparatus of FIG. 9 taken along line 10—10.

FIGS. 7-10 show a sequence of closure for an approximating apparatus substantially similar to that described above with respect to FIGS. 5-6 with the exception that the first and second jaw structure are provided with gripping ends 156, 158 instead of an anvil and staple cartridge. In FIGS. 7-8 the first stationary jaw structure 160 and the second movable jaw structure 162 are disposed in the open position with their respective distal ends, formed as gripping ends 156, 158, spaced apart. Camming housing 144 is driven longitudinally distally such that camming surfaces 146, 148 on the camming housing 144 engage and drive sloped camming surfaces 132, 134, respectively, on the proximal end of the second movable jaw structure 162. This causes the second movable jaw structure 162 to move in substantially parallel approximation motion guided by vertical slots 140, 142 and transverse pins 136, 138. Upon reaching its full longitudinal distal travel (FIGS. 9-10) camming surfaces 146, 148 move onto locking flats 164, 166 formed at the top of the sloped camming surfaces 132, 134. Thus, the gripping ends 156, 158 are maintained in close parallel approximation around subject tissue.

As in previous embodiments, the approximating apparatus of FIGS. 7-10 may be removable from and insertable into a wide variety of actuating means.

Figure 11:
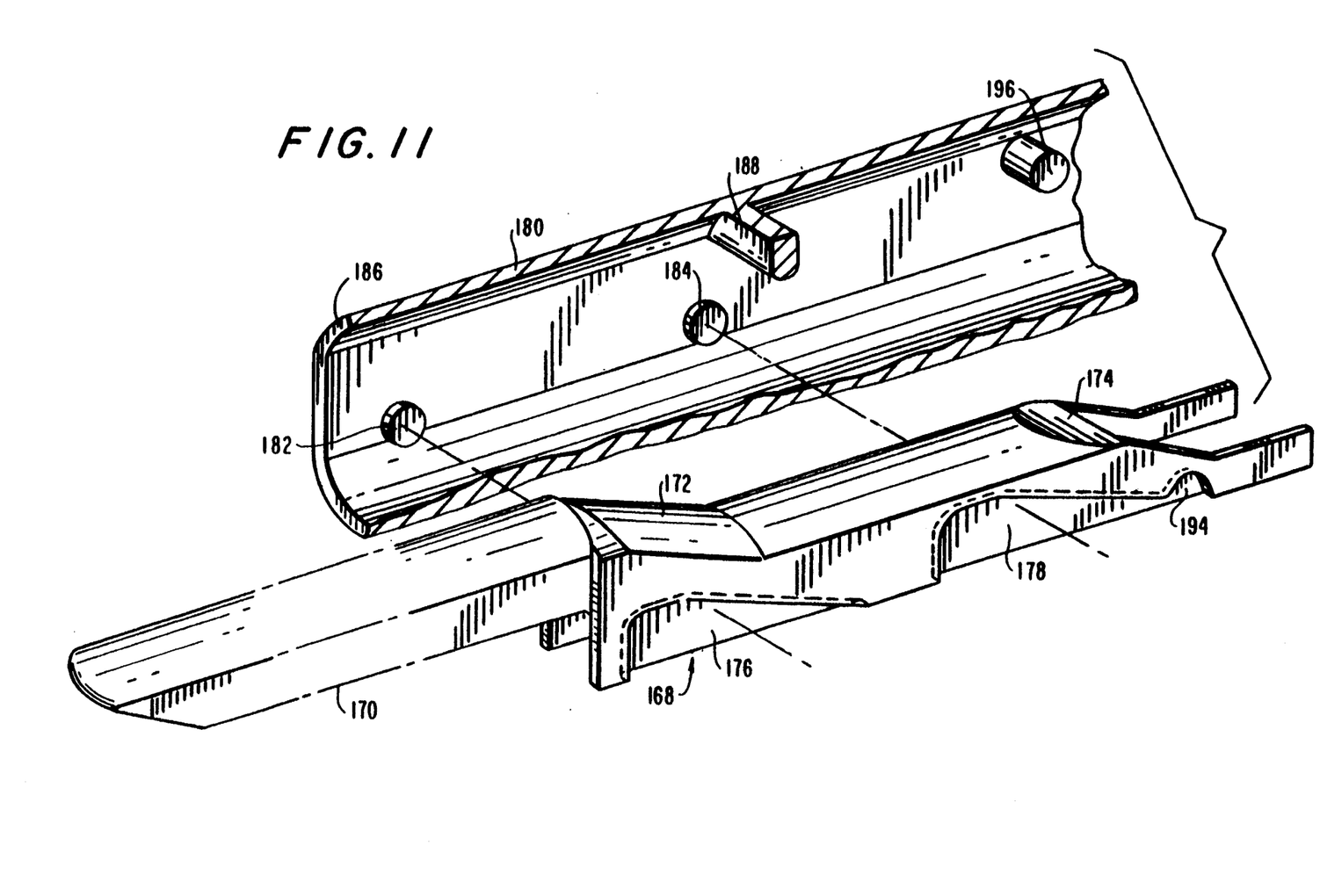
FIG. 11 is a perspective view in partial cross section of apparatus in accordance with the present invention utilizing surgical cleaving jaw structure.

FIGS. 11-14 disclose approximating apparatus in accordance with a preferred embodiment of the present invention utilizing cutting jaw elements. Referring to FIG. 11, a first movable jaw structure 168 is shown including a distal end having cutting structure 170 formed therein and a proximal end having first and second camming surfaces 172, 174 on a top portion thereof and first and second longitudinally disposed camming chambers 176, 178 formed in a sidewall portion thereof. A camming housing or frame 180, shown in cross section in FIG. 11, encloses a portion of the proximal end of the first movable jaw structure 168 and has first and second camming bosses 182, 184 disposed in opposing sidewalls adjacent to first and second camming chambers 176, 178 in first movable jaw structure 168. Camming housing 180 also includes first and second camming surfaces 186, 188 disposed adjacent first and second camming surfaces 172, 174 on the proximal end of the first movable jaw structure (see FIGS. 12-14)

A second stationary jaw structure 190 is disposed within camming housing 180 and interfits with first movable jaw structure 168 for relative substantially parallel approximation therewith. The proximal end of the stationary jaw structure 190 is prevented from rotational motion by locking pin 196. A cutting block 192 is disposed on a distal end of jaw structure 190 for substantially parallel working interaction with cutting structure 170.

Figure 12:
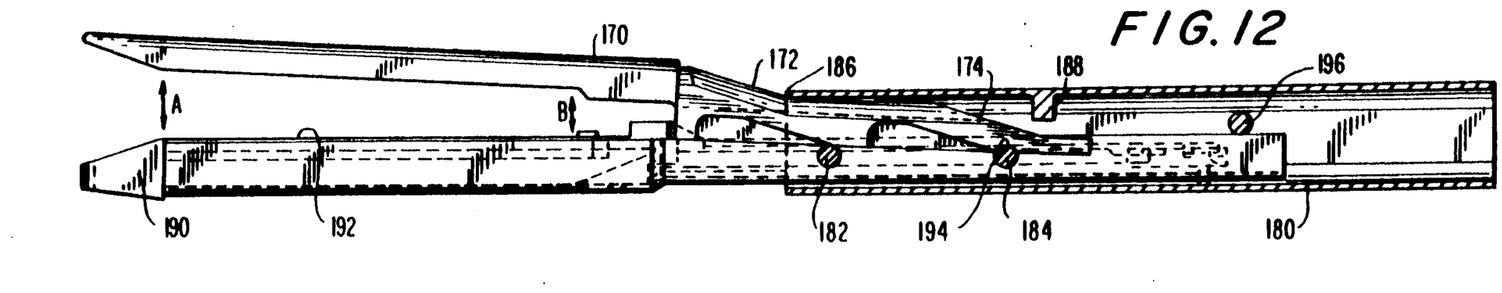
FIG. 12 is a side view in cross section of the apparatus of FIG. 11 in the extended open position.
Figure 13:
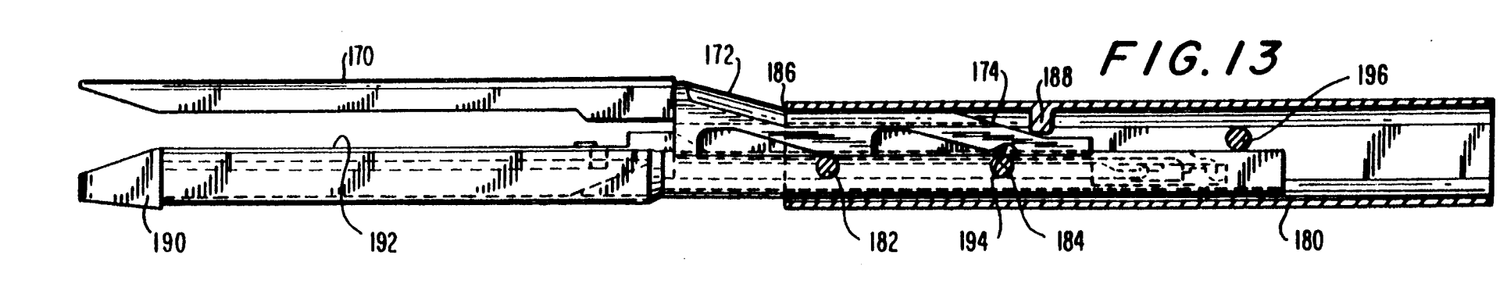
FIG. 13 is a side view in cross section of the apparatus of FIG. 11 in the open position.
Figure 14:
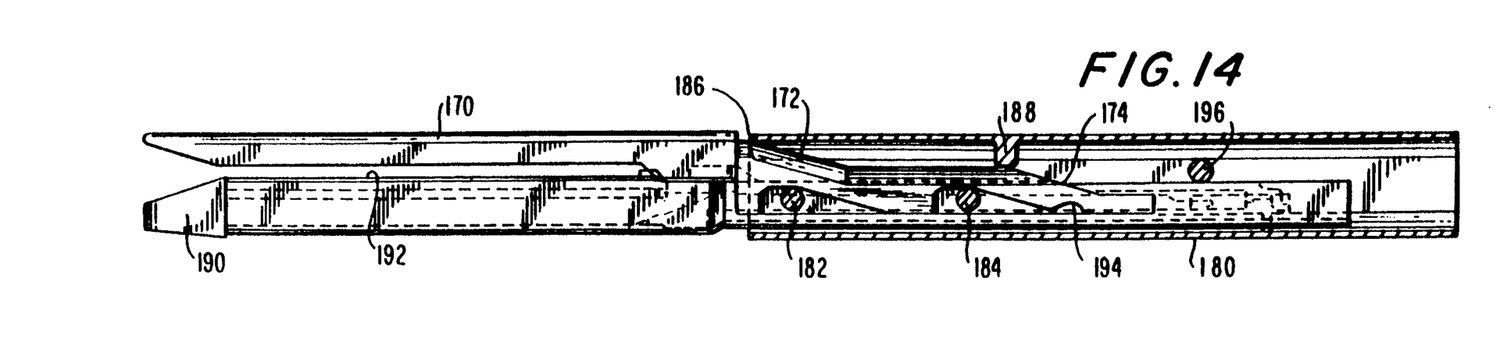
FIG. 14 is a side view in cross section of the apparatus of FIG. 11 in the closed position.

In the embodiment of FIGS. 11-14, first movable jaw structure 168 is initially disposed in an open extended orientation relative to second stationary jaw structure 190 (FIG. 12). First camming bosses 182 are positioned proximally beneath first camming chambers 176 while second camming bosses 184 are disposed in a pivot chamber 194 formed in a proximal portion of second camming chambers 178. As seen in FIG. 12, this configuration allows the opening between the distal ends of cutting structure 170 and cutting block 192 ("A" in FIG. 12) to be wider than the opening between the proximal ends of cutting structure 170 and cutting block 192 ("B" in FIG. 12). Thus initial tissue capture is facilitated.

In operation, camming housing 180 is moved longitudinally distally by actuating means (not shown) relative to first and second jaw structure 168, 190. As the camming housing 180 moves distally, second camming bosses 184 are freed from pivot chamber 194 and camming surfaces 186 and 188 respectively engage camming surfaces 172 and 174 formed in the proximal end of first movable jaw structure 168. This camming engagement effects a substantially parallel approximation of the cutting structure 170 and the cutting block 192 (See FIGS. 13-14). Camming bosses 182, 184 serve to guide this substantially parallel approximation as they travel along the diagonally sloping surface of the first and second camming chambers 176, 178.

This substantially parallel approximation of the jaw structure permits an accurate and controlled separation of the tissue without the uneven and progressive shearing action inherent in conventional scissors structure.

To the extent not already indicated, it also will be understood by those of ordinary skill in the art that any one of various specific embodiments herein described and illustrated may be further modified to incorporate features shown in other of the specific embodiments. For example, first and second jaw structures may both be adapted to move transverse to the longitudinal axis of the device to effect parallel approximation by providing complementary camming means for each jaw structure.

The invention in its broader aspects therefore is not limited to the specific embodiments herein shown and described but departures may be made therefrom within the scope of the accompanying claims without departing from the principles of the invention and without sacrificing its chief advantages.

We claim:

1. Apparatus for approximating jaw structure of surgical instrumentation comprising:
   a tubular endoscopic housing defining a longitudinal axis, a distal end and a proximal end, said housing an axial bore in said distal end;
   first jaw structure extending from distal end of said endoscopic housing and stationary with respect thereto, said first jaw structure having a distal working end and a proximal end;
   second jaw structure disposed in spaced relation to and connected with said first jaw structure, said second jaw structure having a distal working end for substantially parallel working interaction with said first jaw structure and a proximal end, said first and second jaw structure being disposed substantially parallel to the longitudinal axis of the surgical instrumentation and interconnected for substantially parallel approximation; and
   approximating means, at least partially disposed in said axial bore, having camming structure for camming said second jaw structure in substantially parallel relation with respect to said first jaw structure to permit working interaction between said distal working end of said first and second jaw structure, wherein said approximating means includes;
   a camming plate axially slidable within said axial bore, said camming plate having a first and second camming slot formed therein;
   a first camming pin disposed in said first camming slot and transversely mounted in the proximal end of said second jaw structure, said first camming pin engaging transverse slots in said endoscopic housing to restrict axial movement of said distal working end of said second jaw structure;
   a second camming pin disposed in said second camming slot and transversely mounted parallel to said first camming pin in the proximal end of said second jaw structure such that axial movement of said camming plate relative to said endoscopic housing causes substantially parallel approximation of said distal working ends of said first and second jaw structure;

2. Apparatus as in claim 1 wherein said working ends of said first and second jaw structure collectively comprise surgical clamping jaws.

3. Apparatus as in claim 1 wherein said working ends of said first and second jaw structure collectively comprise surgical gripping jaws.

4. Apparatus as in claim 2 wherein at least one of said camming slots includes a substantially axially aligned portion such that when at least one of said camming pins is disposed in said substantially axially aligned portion, said distal working ends of said first and second jaw structure move into non-parallel alignment to facilitate capture of tissue.

5. Apparatus as in claim 1 further comprising actuating means axially disposed in said frame means for driving said camming plate axially therein.

6. Apparatus as in claim 5 further comprising a spring loaded actuating means for axially moving said camming plate to open said distal working ends of said first and second jaw structure in a substantially parallel manner.

7. Apparatus as in claim 1 wherein said first and second jaw structure collectively comprise tissue measuring structure.

8. Apparatus as in claim 1 wherein at least one of said jaw structures extends beyond an outer perimeter of said endoscopic housing when in a substantially open position.

9. Apparatus for approximating jaw structure of surgical instrumentation comprising:
   a tubular endoscopic housing defining a longitudinal axis, a distal end and a proximal end, said housing an axial bore in said distal end;

first jaw structure extending from distal end of said endoscopic housing and stationary with respect thereto, said first jaw structure having a distal working end and a proximal end;

second jaw structure disposed in spaced relation to and connected with said first jaw structure, said second jaw structure having a distal working end for substantially parallel working interaction with said first jaw structure and a proximal end, said first and second jaw structure being disposed substantially parallel to the longitudinal axis of the surgical instrumentation and interconnected for substantially parallel approximation; and approximating means, at least partially disposed in said axial bore, having camming structure for camming said second jaw structure in substantially parallel relation with respect to said first jaw structure to permit working interaction between said distal working ends of said first and second jaw structure, wherein said working ends of said first and second jaw structure collectively comprise tissue measuring structure.

10. Apparatus as in claim 9 further comprising measurement indicating means for displaying a visual measurement of tissue.

11. Apparatus as in claim 9 wherein the tissue measuring structure is adapted to measure tissue compressed between said first and second jaw structure.

12. Apparatus as in claim 9 wherein the tissue measuring structure is adapted to measure tissue surrounding said first and second jaw structure.

13. A method for measuring tissue comprising the steps of:

providing a tissue measuring device having a tubular endoscopic housing defining a longitudinal axis, a distal end and a proximal end, said housing having an axial bore in said distal end, first jaw structure extending from said distal end of said endoscopic housing and stationary with respect thereto, said first jaw structure having a tissue measuring distal working end and a proximal end, second jaw structure disposed in spaced relation to and connected with said first jaw structure, said second jaw structure having a tissue measuring distal working end and a proximal end for substantially parallel working interaction with said tissue measuring distal working end of said first jaw structure, said first and second jaw structure being disposed substantially parallel to the longitudinal axis of the tissue measuring device, and approximating means, at least partially disposed in said axial bore, having camming structure for camming said first and second jaw structure in substantially parallel relation with respect to one another to permit tissue measuring between said tissue measuring distal working ends of said first and second jaw structure;

capturing tissue to be measured by said tissue measuring distal working ends of said first and second jaw structure;

approximating said tissue measuring distal working ends of said first and second jaw structure in substantially parallel relation; and generating a measurement of said captured tissue based upon the relative spatial orientation of said approximated tissue measuring distal working ends of said first and second jaw structure.

14. A method of clamping tissue comprising the steps of:

providing a tissue clamping device having a tubular endoscopic housing defining a longitudinal axis, a distal end and a proximal end, said housing having an axial bore in said distal end, first jaw structure extending from said distal end of said endoscopic housing and stationary with respect thereto, said first jaw structure having a tissue clamping distal working end and a proximal end, second jaw structure disposed in spaced relation to and connected with said first jaw structure, said second jaw structure having a tissue clamping distal working end and a proximal end for substantially parallel working interaction with said tissue clamping distal working end of said first jaw structure said first and second jaw structure being disposed substantially parallel to the longitudinal axis of the tissue clamping device, and approximating means, at least partially disposed in said axial bore, having camming structure for camming said first and second jaw structure in substantially parallel relation with respect to one another to permit tissue clamping between said tissue clamping distal working ends of said first and second jaw structure;

capturing tissue to be clamped by said tissue clamping distal working ends of said first and second jaw structure;

approximating said tissue clamping working ends of said first and second jaw structure in substantially parallel to clamp said captured tissue.

15. A method for gripping tissue comprising the steps of:

providing a tissue gripping device having a tubular endoscopic housing defining a longitudinal axis, a distal end and a proximal end, said housing having an axial bore in said distal end, first jaw structure extending from said distal end of said endoscopic housing and stationary with respect thereto, said first jaw structure having a tissue gripping distal working end and a proximal end, second jaw structure disposed in spaced relation to and connected with said first jaw structure, said second jaw structure having a tissue gripping distal working end and a proximal end for substantially parallel working interaction with said tissue gripping distal working end of said first jaw structure said first and second jaw structure being disposed substantially parallel to the longitudinal axis of the tissue gripping device, and approximating means, at least partially disposed in said axial bore, having camming structure for camming said first and second jaw structure in substantially parallel relation with respect to one another to permit tissue gripping between said tissue gripping distal working ends of said first and second jaw structure;

capturing tissue to be gripped by said tissue gripping distal working ends of said first and second jaw structure; and approximating said tissue gripping distal working ends of said first and second jaw structure in substantially parallel relation to grip said captured tissue.

* * * * *